United States Patent
Smith et al.

(10) Patent No.: US 11,202,918 B2
(45) Date of Patent: Dec. 21, 2021

(54) EYE TREATMENT SYSTEM

(71) Applicant: Edinburgh Biosciences Limited, Livingston (GB)

(72) Inventors: Desmond Smith, Livingston (GB); Alan Kerr, Livingston (GB)

(73) Assignee: Edinburgh Biosciences Limited

( * ) Notice: Subject to any disclaimer, the term of this patent is extended or adjusted under 35 U.S.C. 154(b) by 224 days.

(21) Appl. No.: 16/064,347

(22) PCT Filed: Dec. 1, 2016

(86) PCT No.: PCT/GB2016/053780
§ 371 (c)(1),
(2) Date: Jun. 20, 2018

(87) PCT Pub. No.: WO2017/109454
PCT Pub. Date: Jun. 29, 2017

(65) Prior Publication Data
US 2018/0353769 A1    Dec. 13, 2018

(30) Foreign Application Priority Data

Dec. 21, 2015 (GB) ...................................... 1522555

(51) Int. Cl.
*A61N 5/06* (2006.01)
*A61B 3/10* (2006.01)
(Continued)

(52) U.S. Cl.
CPC .............. *A61N 5/0613* (2013.01); *A61B 3/10* (2013.01); *A61B 3/1176* (2013.01);
(Continued)

(58) Field of Classification Search
None
See application file for complete search history.

(56) References Cited

U.S. PATENT DOCUMENTS

| 5,894,340 A | 4/1999 | Loree et al. |
| 2003/0112409 A1 | 6/2003 | Vaughn et al. |

(Continued)

FOREIGN PATENT DOCUMENTS

| WO | 2010/097582 | 9/2010 |
| WO | 2010097582 A1 | 9/2010 |

(Continued)

OTHER PUBLICATIONS

Kessel et al., "Non-Invasive Bleaching of the Human Lens by Femtosecond Laser Photolysis", PLOS One, vol. 10 Apr. 2015.

(Continued)

*Primary Examiner* — Ankit D Tejani
(74) *Attorney, Agent, or Firm* — Fresh IP PLC; Clifford D. Hyra; Aubrey Y. Chen

(57) ABSTRACT

A system (1) for treating and monitoring the condition of an eye (6) includes a light source, preferably a non-lasing LED (2), for irradiating the eye at a wavelength sufficient to reverse eye damage. The system also includes an excitation light source, preferably a non-lasing LED (4), for exciting fluorescence in the eye and a detector (22) for detecting fluorescence stimulated by the excitation LED (4). The system may also include a second non-lasing light source, preferably a non-lasing LED, for irradiating the eye; and a detector for detecting scatter of light from the eye. Methods for monitoring, diagnosis and treatment of eye conditions such as cataracts are also provided.

13 Claims, 10 Drawing Sheets

(51) Int. Cl.
*A61B 3/117* (2006.01)
*A61F 9/007* (2006.01)
(52) U.S. Cl.
CPC .......... *A61F 9/0079* (2013.01); *A61N 5/0601* (2013.01); *A61N 2005/063* (2013.01); *A61N 2005/0612* (2013.01); *A61N 2005/0651* (2013.01); *A61N 2005/0661* (2013.01); *A61N 2005/0662* (2013.01)

(56) References Cited

U.S. PATENT DOCUMENTS

| | | | |
|---|---|---|---|
| 2004/0189939 A1* | 9/2004 | Dick | A61F 9/00804 351/209 |
| 2006/0235493 A1 | 10/2006 | Dotson | |
| 2010/0262016 A1* | 10/2010 | Imanishi | A61B 3/1025 600/473 |
| 2011/0202114 A1* | 8/2011 | Kessel | A61F 9/008 607/88 |
| 2012/0083772 A1 | 4/2012 | Rubinfeld et al. | |
| 2013/0301004 A1* | 11/2013 | Kahn | A61B 3/10 351/206 |
| 2015/0109579 A1* | 4/2015 | Orlowski | G06T 7/337 351/206 |
| 2016/0073876 A1* | 3/2016 | Akita | A61B 3/0058 351/206 |
| 2017/0182191 A1* | 6/2017 | Towne | A61N 5/0601 |

FOREIGN PATENT DOCUMENTS

| | | |
|---|---|---|
| WO | 2011044589 A2 | 4/2011 |
| WO | 2015/101785 | 7/2015 |
| WO | 2015101785 A1 | 7/2015 |

OTHER PUBLICATIONS

Holm et al., "Effect of photobleaching on selected advanced glycation end products in the human lens", BMC Research Notes, vol. 8, Jan. 2015.
Kessel et al., "Action Spectrum for Photobleaching of Human Lenses by Short Wavelength Visible Irradiation", PLOS One, vol. 5 Issue 3, Mar. 2015.
D.M.Gakamsky et al., "Exploring the Possibility of Early Cataract Diagnostics based on Tryptophan Fluorescence", Journal of the Royal Society Interface, vol. 8, 2011, pp. 1616-1621.
Search Report dated May 12, 2016 in GB Patent Application No. GB1522555.0.
International Search Report dated Feb. 16, 2017 in International Application PCT/GB2016/053780 filed Dec. 1, 2016.

* cited by examiner

EYE TREATMENT SYSTEM

FIELD OF THE INVENTION

The present invention relates to a non-invasive system and method for treating and monitoring changes in cataract or cataract formation using intrinsic fluorescence reporters of the eye lens proteins, light scattering, and LED photobleaching.

BACKGROUND OF THE INVENTION

Early diagnosis of cataracts is non-trivial and is currently insufficient, as diagnosis is carried out via visual inspection of the lens. This has prompted investigation of early detection methods. Recent research suggests that fluorescence could be used to diagnose and monitor cataracts.

WO2010/097582 describes a tryptophan-based method for detecting changes in a human or animal eye. The method involves illuminating the eye or at least a part thereof, in particular the lens and/or cornea, using light at a tryptophan red edge excitation wavelength and detecting tryptophan fluorescence. The detected tryptophan fluorescence is used to detect or identify structural defects or changes in the eye, such as the formation of cataracts.

WO2015/101785 describes another tryptophan-based method for detecting changes in a human or animal eye. In this case, the eye lens is illuminated to cause fluorescence. Features in the fluorescence associated with tryptophan and at least one of its photo-products are used to quantify or grade modifications and/or structural defects in the lens.

One of the photo-products of tryptophan that can be useful to quantify or grade modifications and/or structural defects in the lens is kynurenine, in particular N-Formylkynurenine (NFK). The fluorescence properties of kynurenine can detect the presence of cataracts. For example, over time, as aggregation increases, intrinsic tryptophan fluorescence emission (at 340 nm) intensity decreases as the tryptophan is converted to NFK (at 430 nm), and so the NFK fluorescence emission increases.

"Non-Invasive Bleaching of the Human Lens by Femtosecond Laser Photolysis" by Line Kessel et al, www.plosone.org, 1 Mar. 2010, Volume 5, Issue 3, e9711 describes a method for treating the human eye using a femtosecond laser with an output wavelength centred on 800 nm, and a two photon absorption process. The results described in this paper demonstrate that age-induced yellowing of the human lens can be bleached using femtosecond laser photolysis.

SUMMARY OF THE INVENTION

According to one aspect of the present invention, there is provided a system for treating and monitoring the condition of an eye, the system comprising a non-lasing light source, preferably a non-lasing LED, for irradiating the eye at a wavelength sufficient to reverse eye damage, an excitation light source, preferably a non-lasing LED, for exciting fluorescence in the eye and a detector for detecting fluorescence stimulated by the excitation light source.

Preferably, the irradiating light source is a non-lasing LED that emits light of a wavelength 405 nm.

The excitation light source may be at least one non-lasing LED operable to emit light at a wavelength in the range 310 nm to 370 nm, preferably 310 nm to 365 nm. Preferably, the excitation light source is a non-lasing LED that emits light of a wavelength 360 nm. The bandwidth of the non-lasing LEDs is typically 20 nm. If desired the bandwidth may be narrowed, for example by use of an interference filter.

The wavelength of the irradiating light may be in the range of 400 to 515 nm. Preferably, the wavelength of the irradiating light is 405 nm or 420 nm. The bandwidth of the non-lasing LEDs is typically 20 nm.

Irradiation of the eye with light of a wavelength sufficient to reverse eye damage, for example at 405 nm or 420 nm, may be done simultaneously with excitation using the excitation LED, for example at 360 nm. Using light at 360 nm for fluorescence excitation avoids absorption problems associated with the cornea.

According to another aspect of the present invention, there is provided a method for treating cataracts, the method comprising irradiating the eye at a wavelength sufficient to reverse eye damage using a non-lasing light source, for example a non-lasing LED.

Preferably, the wavelength of the irradiating light is in the range of 400 to 515 nm. Preferably, the wavelength of the irradiating light is 405 nm or 420 nm.

According to still another aspect of the invention, there is provided a system for treating cataracts comprising a non-lasing light source, such as an LED for irradiating the eye at a wavelength sufficient to reverse eye damage using a non-lasing light source.

The wavelength of the irradiating light may be in the range of 400 to 520 nm, for example in the range 405 to 515 nm, for example 405 nm or 420 nm.

According to still another aspect of the invention, there is provided a non-lasing light source, such as a non-lasing LED, for use in the treatment of cataracts. The non-lasing light source may be operable to emit light in range of 400 to 520 nm, for example in the range 405 to 515 nm, for example 405 nm or 420 nm.

According to still another aspect of the invention, there is provided a non-lasing light source such as an LED, for use in the treatment of cataracts, wherein the treatment involves single photon absorption. The non-lasing light source may be operable to emit light in range of 400 to 520 nm, for example in the range 405 to 515 nm, for example 405 nm or 420 nm.

The irradiation with one or more non-lasing light sources, such as an LED, to monitor and treat an eye as described herein may be achieved by irradiating the eye, in particular the lens of the eye, from an external location in a non-invasive manner i.e. without employing a surgical technique.

However, as an alternative that may be suitable where the cornea of the eye is less transparent to light at the selected wavelengths, insertion of a probe into the eye tissue is contemplated.

Thus a system for treating and monitoring the condition of an eye as described herein may include a probe comprising a light guide, preferably an optical fibre light guide, to transmit light into and/or receive light from the lens of an eye in use. The light guide is connected to the optical system delivering the light from the non-lasing light sources and delivering the light to the detector.

Thus a system for treating cataracts as described herein may include a probe comprising a light guide, preferably an optical fibre light guide, to transmit light into and/or receive light from the lens of an eye in use.

Thus a method for treating cataracts as described herein may include insertion into an eye of a probe comprising a light guide, preferably an optical fibre light guide, to transmit light into and/or receive light from the lens of an eye.
}

Thus a non-lasing light source, such as a non-lasing LED, for use in the treatment of cataracts as described herein may include a probe comprising a light guide, preferably an optical fibre light guide, to transmit light into and/or receive light from the lens of an eye in use.

Thus a non-lasing light source such as an LED, for use in the treatment of cataracts, wherein the treatment involves single photon absorption of the lens tissue, may include a probe comprising a light guide, preferably an optical fibre light guide, to transmit light into and/or receive light from the lens of an eye in use.

A probe comprising a light guide will typically be inserted into eye tissue so as to allow light to directly irradiate the lens e.g. the probe is inserted into the lens or at least through the cornea to the outer surface of the lens. This may be achieved by known surgical techniques, such as those employed to insert an ultrasonic probe into an eye lens during cataract surgery where phacoemulsification is employed to break up the lens. Thus an incision may be made into the cornea and typically also the lens capsule to give direct access to the lens for the end of the probe.

Where the light guide is an optical fibre light guide the end of a typical optical fibre light guide has been shown capable of transmitting light over a wide angle and to receive light from a wide angle, convenient for treating and/or monitoring at least a substantial part of the lens without being moved.

The same technique may be used as a research tool on in vitro whole eyes or eye tissue including the cornea. For example where it is desired to illuminate the lens or receive fluorescence or scattered light from the lens more or less directly, without light passing through other eye tissue.

A relatively fine optical fibre may be employed. An optical fibre of a diameter of about 200 μm can be directed to provide good illumination of an eye lens and so as to avoid excessive illumination of the retina. The end of the optical fibre light guide may include a lens to direct the light as desired.

According to still another aspect of the invention there is provided a system for monitoring the condition of an eye, the system comprising a non-lasing light source, preferably a non-lasing LED, for irradiating the eye; and a detector for detecting scatter of light from the eye.

The system detecting scatter may be a stand-alone system. This is convenient for testing of an eye, for example it may be employed before more extensive monitoring and/or treatment is carried out.

Alternatively the system may be incorporated into the system for treating and monitoring the condition of an eye, according to the first mentioned aspect of the invention discussed above.

Thus such a system comprises:
a non-lasing light source, preferably a non-lasing LED, for irradiating the eye at a wavelength sufficient to reverse eye damage;
an excitation a light source, preferably a non-lasing LED, for exciting fluorescence in the eye;
a detector for detecting fluorescence stimulated by the excitation LED; and
a second non-lasing light source, preferably a non-lasing LED, for irradiating the eye; and a detector for detecting scatter of light from the eye.

Where the system for detecting scatter is employed as part of such a system for treating and monitoring the condition of an eye, according to the first mentioned aspect of the invention then preferably the second non-lasing light source is a separate LED source at an angle away from the normal of the incident light from the excitation light source and the irradiating light source for use in reversing eye damage.

Preferably, the non-lasing light source for a system that detects scatter is a non-lasing LED that emits light of a wavelength of from 450 nm to 550 nm.

The scatter of light is detected for example by a diode detector. The detector may be rotatable about the position of an eye in use, to measure scatter at different angles with respect to the direction of irradiation from the non-lasing light source.

For use on an in vivo eye, the detector will measure back scatter.

The scatter of light may also be used as a research technique on in vitro tissue. For example whole eyes may be examined using backscatter. The system may also be used for research involving parts of eyes such as eye lenses or lens and cornea combined. Such parts of eyes may be examined by measuring through scatter.

Light scatter from the lens of an eye may give a measure of the extent of fogging due to development of a defect such as a cataract. Light scatter has been shown capable of observing the photobleaching effect achievable by use of a non-lasing light source such as an LED as described herein.

Light scatter may be measured in terms of at least one of: power of the scattered light; and the angular width of scattered light with respect to the direction of irradiation from the non-lasing light source. The results may be provided as a graph of power to angle with respect to the direction of irradiation from the non-lasing light source. Light scatter may be measured in terms of the width of the scatter peak at half maximum height on the graph of power to angle with respect to the direction of irradiation from the non-lasing light source.

It has been shown that a lens with an induced cataract exhibits stronger scatter and a wider angle of scatter than the fresh lens, before inducing the cataract. Following a photobleaching procedure as described herein, the same lens exhibits a reduction in the power and the angular width of scattered light, returning towards the test results for the fresh lens.

Thus according to still another aspect of the invention there is provided a method for monitoring the condition of an eye, the method comprising irradiating the eye with a non-lasing light source, preferably a non-lasing LED, and determining scatter of light from the eye.

Scatter of light is determined by means of a detector, such as a diode detector. The results from the detector may be provided to a user. The results may be provided in terms of the power of light scattered at one or more angles with respect to the direction of irradiation from the non-lasing light source. The results may be provided as a graph of power to angle with respect to the direction of irradiation from the non-lasing light source.

The results provided to a user from the detector may assist in diagnosis of an eye condition, such as the presence and/or extent of a cataract.

Thus according to still another aspect of the invention there is provided a method for diagnosis of an eye condition, the method comprising irradiating the eye with a non-lasing light source, preferably a non-lasing LED, and determining scatter of light from the eye. Scatter of light is determined by means of a detector. The diagnosis may be aided by comparison of the scatter results with previous scatter results from the same eye and/or with results expected for an eye with a known condition. The diagnosis may be in respect of the presence and/or the extent of a cataract.

BRIEF DESCRIPTION OF THE DRAWINGS

Various aspects of the invention will now be described by way of example only, with reference to the accompanying drawings, of which.

DETAILED DESCRIPTION OF THE DRAWINGS

Figure 1:
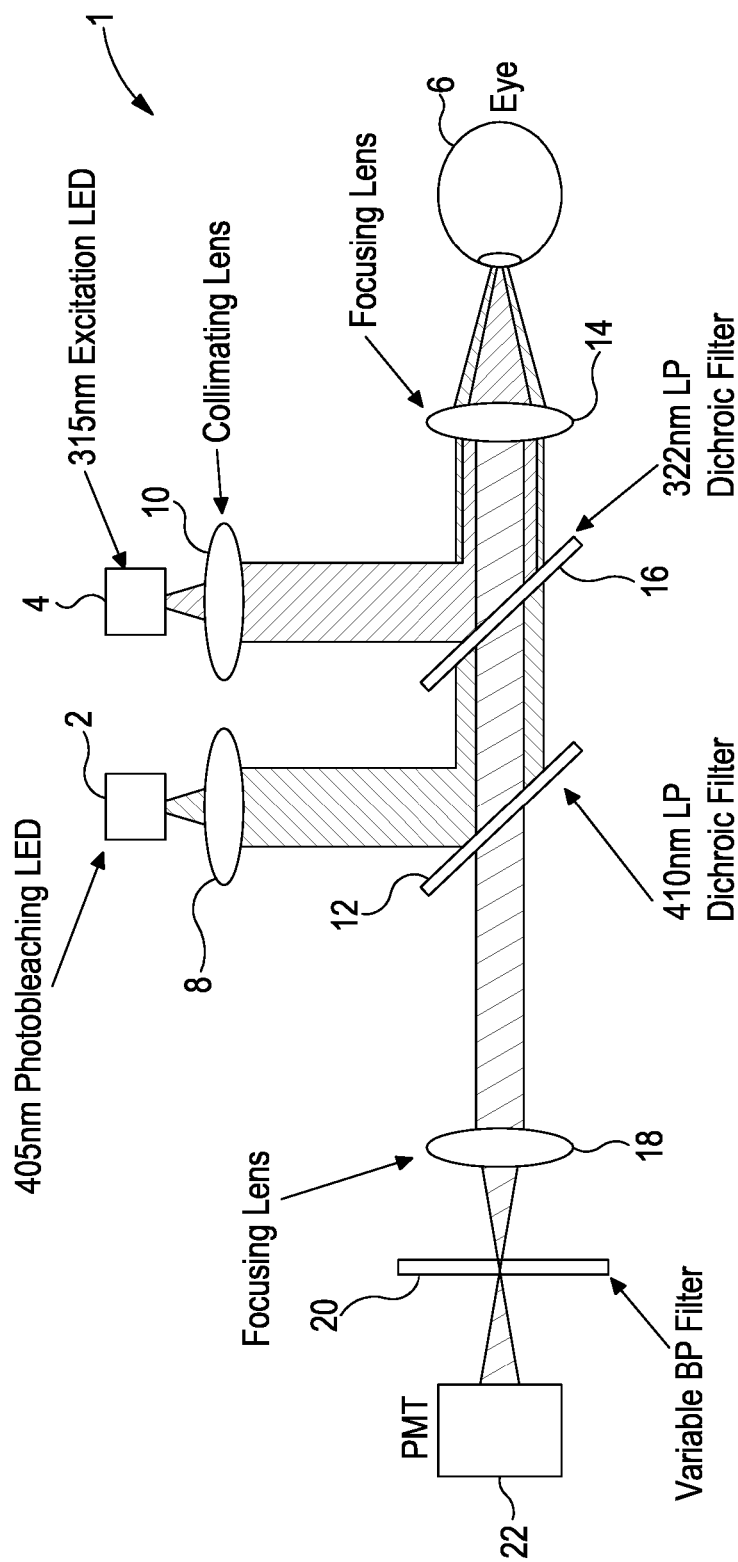
FIG. 1 is a schematic diagram of an optical system for treating and monitoring an eye.

FIG. 1 shows a system 1 for treating and monitoring changes in cataract or cataract formation using light. This has a single photon treatment/photobleaching (non-lasing) LED 2 that emits light at 405 nm. This LED is used for treating the eye. An excitation (non-lasing) LED 4 is also provided. This emits light at 315 nm for monitoring the condition of the eye 6.

Collimating lenses 8,10 are provided for collimating light from each of the photobleaching LED 2 and the excitation LED 4. Light from the photobleaching LED 2 is directed onto a short pass dichroic beam splitter 12 (in this case a 410 nm dichroic beam splitter) that is adapted to reflect the treatment light along an optical path to a first focusing lens 14 that focuses the light onto the eye 6. Light from the excitation LED 4 is directed onto a long pass dichroic beam splitter 16 (in this case a 322 nm dichroic beam splitter) that is adapted to reflect the excitation light along the same optical path to the first focusing lens 14 that focuses the light onto the eye 6. The arrangement is on-axis.

The excitation light causes fluorescence of tryptophan and at least one of its photo-products. Fluoresced light is directed along the on-axis optical path through the first focusing lens 14, both of the dichroic beam splitters 12,16 and onto a second focusing lens 18. Positioned at the focal point of the second focusing lens is a variable bandpass filter (BP) 20, for example an interference filter. In a preferred example, the interference filter is a wedge type filter. This is used to selectively pass only fluoresced light to a photomultiplier detector (PMT) 22. The detected fluoresced light can be used to detect changes in the structure of the eye. Techniques for doing this are described, for example, in WO2010097582 and WO2015/101785, the contents of which are incorporated herein by reference.

As an alternative fluorescence detection system, in systems of the invention, the second focussing lens 18 may be replaced by a divergent lens; and the variable bypass filter and photomultiplier detector 22 replaced by a linear variable bandpass filter and a diode array of detectors. The divergent lens can illuminate the whole of the linear variable bandpass filter to allow all wavelengths to be analysed simultaneously by the diode array.

As an example, structural changes in a human or animal eye lens can be detected by detecting fluorescence of tryptophan, its photo-products and other fluorescent post-translational modifications, wherein the fluorescence is caused by simultaneous excitation at the same wavelength in the excitation wavelength range of 305-320 nm. This is at the red edge of the tryptophan absorption band. Examples of tryptophan photo-products are 5-Hydroxytryptophan (5OH-Trp), N-Formylkynurenine (NFK), Kynurenine (Kyn) and 3-Hydroxykynurenine (3OH-Kyn). Examples of other fluorescent PTMs are Argpyrimidine and Pentosidine.

Fluorescence is a relative characteristic and its intensity is a function of experimental parameters, such as intensity of excitation light, excitation and emission wavelength, geometrical and other experimental factors. Simultaneously monitoring emission of individual spectral components of tryptophan photo-products and other fluorescent post-translational modifications associated with eye lens proteins using the same wavelength and intensity of excitation light in the same instrument, upon the same experimental geometry allows determination of concentrations of tryptophan photoproducts and other fluorescent post-translational modifications in eye lens proteins. Conversion of tryptophan side chains to the photo-products decreases tryptophan concentration and increases concentration of its derivatives. The shape of the spectra contains information on the condition of the eye, in particular a measure of the amount of cataract. Variations in the shape of the spectra can be detected using the variable bandpass interference filter.

In a preferred example, the intrinsic tryptophan emission, which has a 340 nm peak, and the intrinsic NFK emission, which is a photoproduct of tryptophan and has a 430 nm emission peak, are monitored. NFK and the 430 nm peak are characteristic of lenses with cataract. In a damaged eye, the intensity of the 340 nm emission peak is reduced below that expected for a healthy eye, and the intensity of the 430 nm emission peak is increased. When treatment of a cataract damaged eye is effective, the intensity of the 340 nm emission peak is increased, and the intensity of the 430 nm emission peak is reduced.

In use, a patient who has cataracts can be treated using simple light from a non-lasing LED, and the treatment can be simultaneously monitored using the non-lasing excitation light from the excitation LED and tracking the resultant fluorescence. By monitoring the intensity of the 340 nm emission peak, and the intensity of the 430 nm emission peak progress of the treatment can be assessed.

To demonstrate the effectiveness of the system of FIG. 1 a healthy porcine lens was extracted and irradiated to cause the formation of cataract. This was done using an excitation monochromator. The lens was irradiated for 21 hours at 310 nm to induce 'cataract'. Irradiation was carried out using a bandwidth of 5 nm. After damage was induced in the extracted porcine lens, fluorescence measurements were acquired by switching on the excitation LED at 315 nm and collecting fluoresced light at the photomultiplier detector. Both the excitation and emission bandwidths were 2 nm for the fluorescence measurements. These fluorescence measurements provide an indication of the start condition of the lens. The photobleaching LED was then switched on, so that light of 405 nm was incident on the eye. Photobleaching causes a spectral return of the lens towards its initial condition. After a predetermined time, the photobleaching LED was switched off. Then the excitation LED was switched on and fluorescence collected at the photo multiplier.

Figure 2:
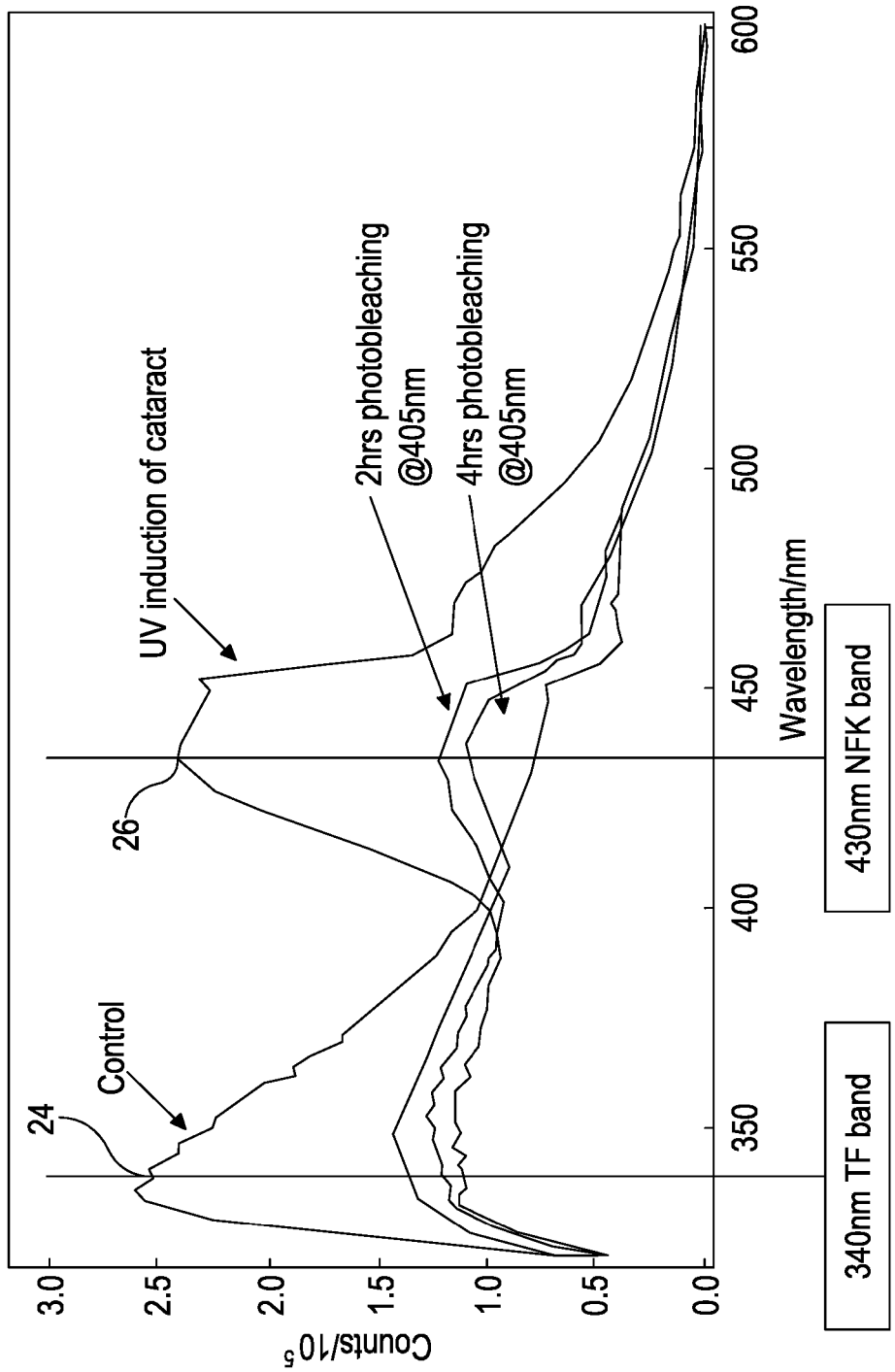
FIG. 2 shows emission spectra stimulated using excitation at 315 nm of an undamaged porcine lens; the lens after cataract formation induced using 310 nm radiation, and the lens after bleaching of the cataract using 405 nm radiation.

FIG. 2 shows the spectra collected at various stages of the process. These show that a peak 24 at 340 nm was observed before irradiation. This is the tryptophan (TF) emission peak. Also, a peak 26 at 430 nm was observed before irradiation, which corresponds to the naturally occurring kynurenines within the lens. Following irradiation at 310 nm a 156% increase in emission intensity was observed at 430 nm indicating the photo-oxidation of tryptophan to NFK and kynurenine. Bleaching of this emission was carried out at 405 nm and induced a 30% decrease in emission intensity. At this stage, there is a reduction in the 430 nm band and an increase in the 340 nm tryptophan band. This demonstrates that the treatment at 405 nm reversed at least some of the damage.

The 405 nm LED is an extremely effective single-photon-bleaching source. This is indicated by the significant drop in the NFK 430 nm within the first 1-2 hours of photobleaching. In general, it was found photo-bleaching with shorter wavelengths appeared to produce a more significant overall drop in the 430 nm NFK band. Using LED sources has the advantage of being able to control the output power from the source and allow irradiation of the sample using much higher output powers than is typically available from a monochromator.

It should be noted that a "good" eye is characterised by a clear tryptophan band at 340 nm. In tests, a good, undamaged lens was irradiated extensively at 405 nm (a photobleaching wavelength). No change in the fluorescence of the good eye was observed. Hence, the 405 nm photobleaching is highly specific to damaged regions of the eye, and causes no damage to normal eye tissue.

Figure 3:
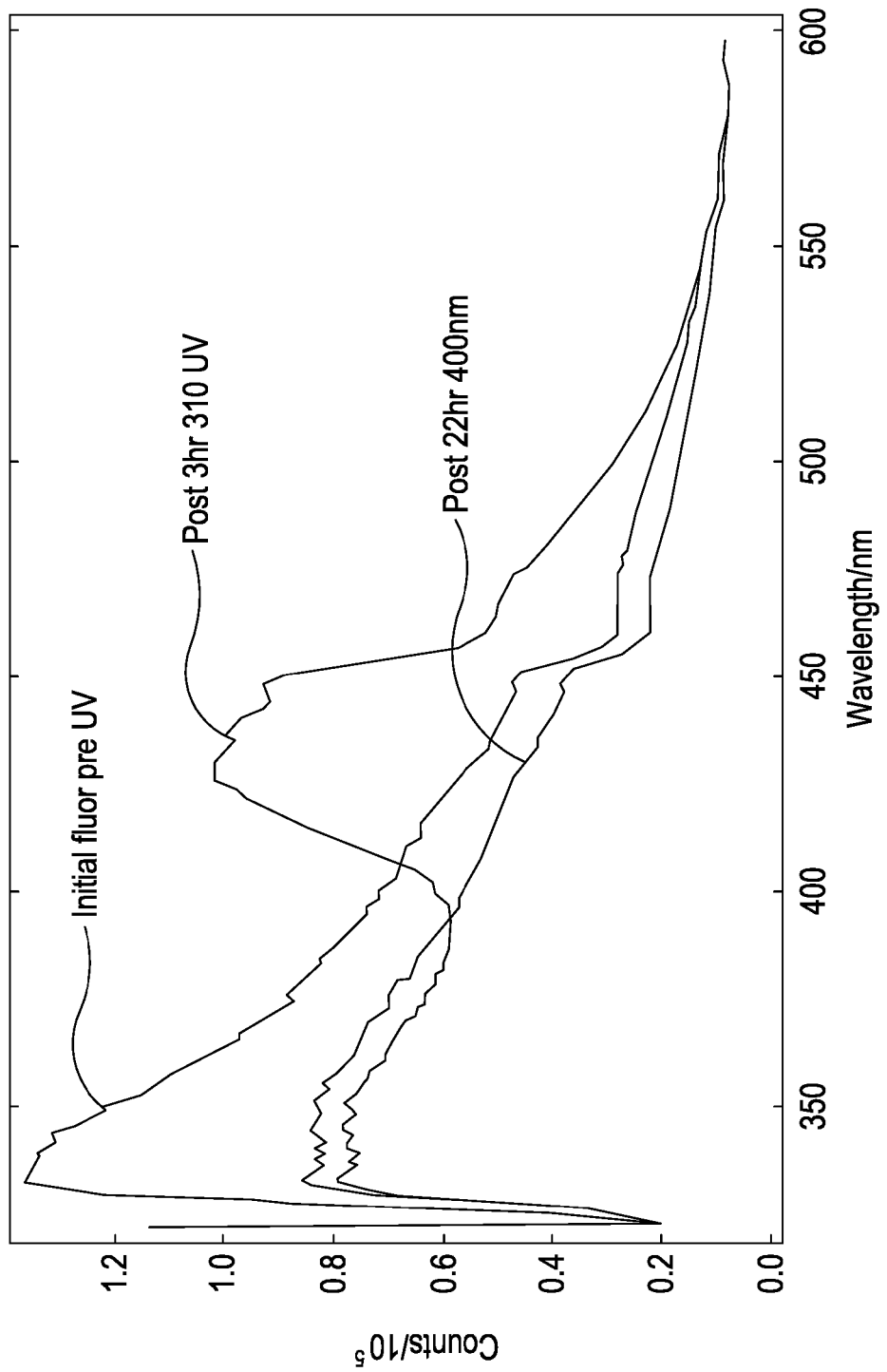
FIG. 3 shows emission spectra stimulated using excitation at 315 nm of an undamaged porcine lens; the lens after cataract formation induced using 310 nm radiation, and the lens after bleaching of the cataract using 400 nm radiation.

Various single photon photobleaching wavelengths can be used. FIG. 3 shows various fluorescence spectral profiles before and after photo-bleaching using a 400 nm irradiation wavelength. As before, the fluorescence excitation wavelength used was 315 nm. In this case, the lens was initially irradiated for 3 hrs with 6 mW of UV light at 310 nm and an excitation bandwidth of 20 nm ('post 3 hr 310 UV'). The lens was then photo-bleached for 22 hrs with 11 mW of 400 nm at an excitation bandwidth of 20 nm ('post 22 hr 400 nm'). This resulted in an approximately 50% decrease in the NFK 430 nm band, and an approximately 8% increase in the tryptophan 340 nm band.

Figure 4:
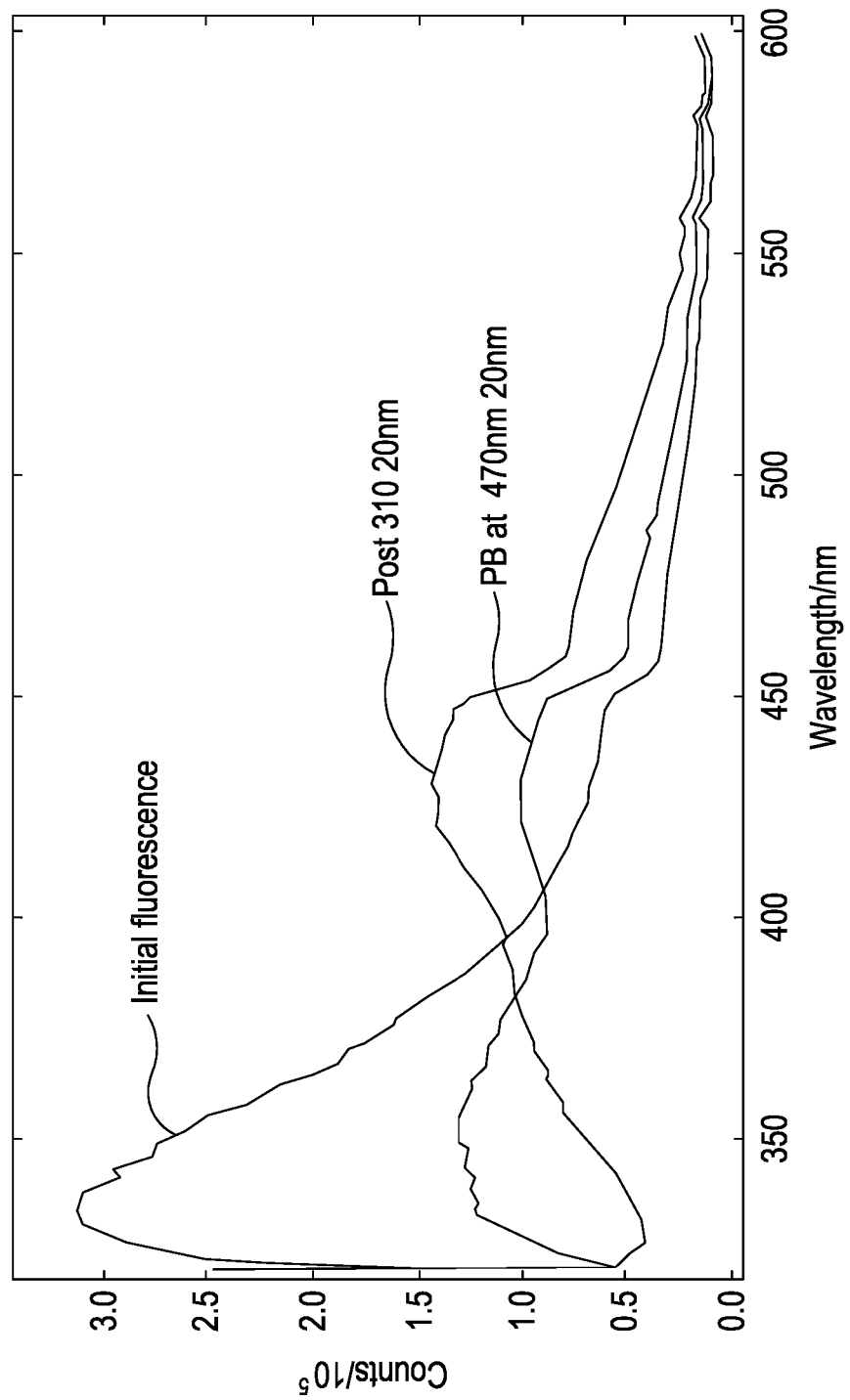
FIG. 4 shows emission spectra stimulated using excitation at 315 nm of an undamaged porcine lens; the lens after cataract formation induced using 310 nm radiation, and the lens after bleaching of the cataract using 470 nm radiation.

FIG. 4 shows various fluorescence spectral profiles before and after photo-bleaching using a 470 nm irradiation wavelength. As before, the fluorescence excitation wavelength used was 315 nm. To cause damage, the lens was initially irradiated for 3 hrs with 6 mW of UV light at 310 nm and an excitation bandwidth of 20 nm ('Post 310 nm 20 nm'). The lens was then photo-bleached for 94 hrs with 9 mW of 470 nm at an excitation bandwidth of 20 nm ('PB at 470 nm 20 nm'). This resulted in an approximately 33% decrease observed in NFK 430 nm band and an approximately 57% increase in the tryptophan 340 nm band.

Figure 5:
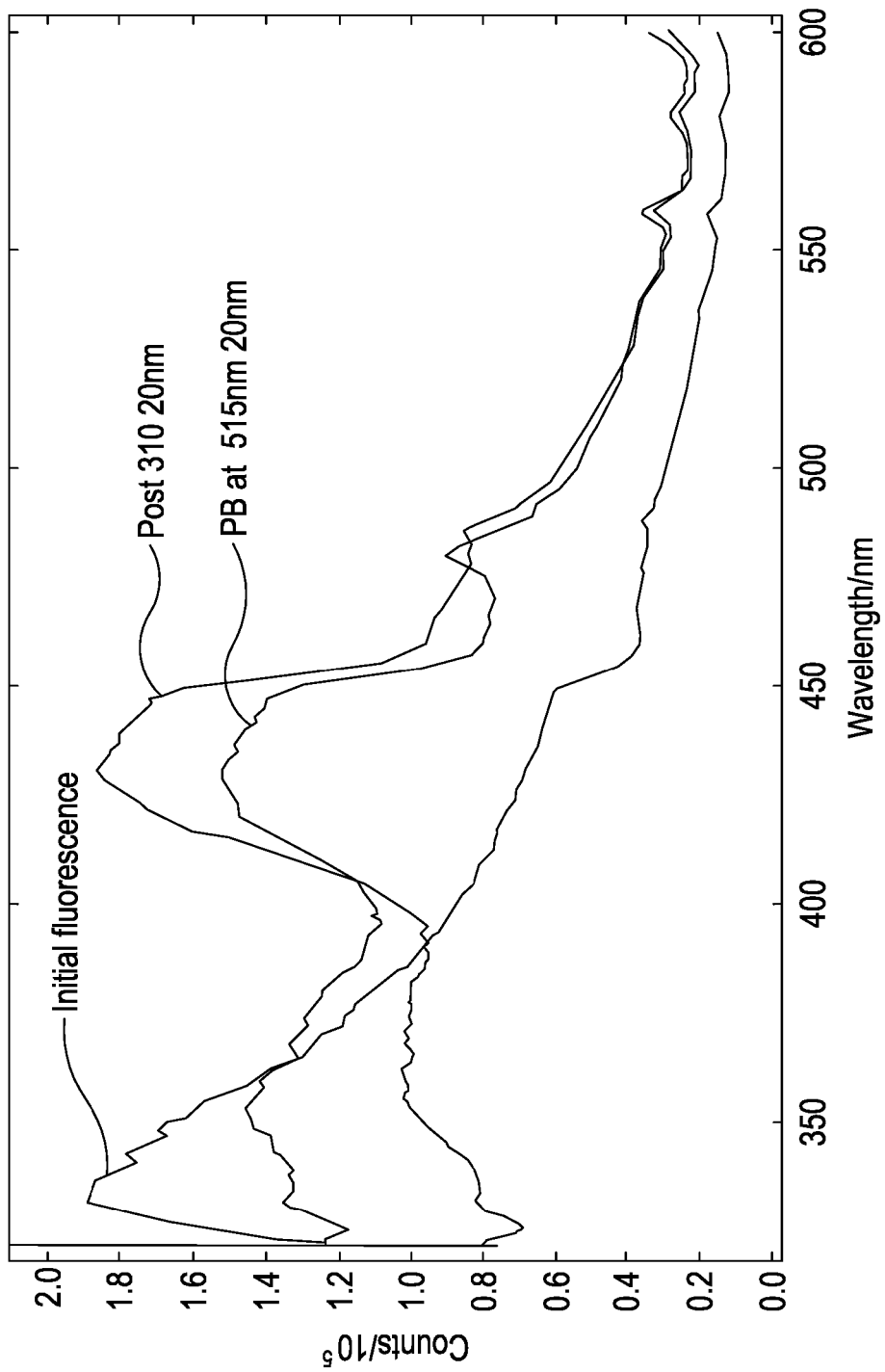
FIG. 5 shows emission spectra stimulated using excitation at 315 nm of an undamaged porcine lens; the lens after cataract formation induced using 310 nm radiation, and the lens after bleaching of the cataract using 530 nm radiation.

FIG. 5 shows various fluorescence spectral profiles before and after photo-bleaching using a 515 nm irradiation wavelength. As before, the fluorescence excitation wavelength used was 315 nm. In this case, the lens was initially irradiated for 3 hrs with 6 mW of UV light at 310 nm and an excitation bandwidth of 20 nm ('post 310 20 nm'). The lens was then photo-bleached for 18 hrs with 10 mW of 515 nm at an excitation bandwidth of 20 nm ('PB at 515 nm 20 nm'). This resulted in almost no change in NFK 430 nm band and an approximately 20% increase in the tryptophan 340 nm band.

Figure 6:
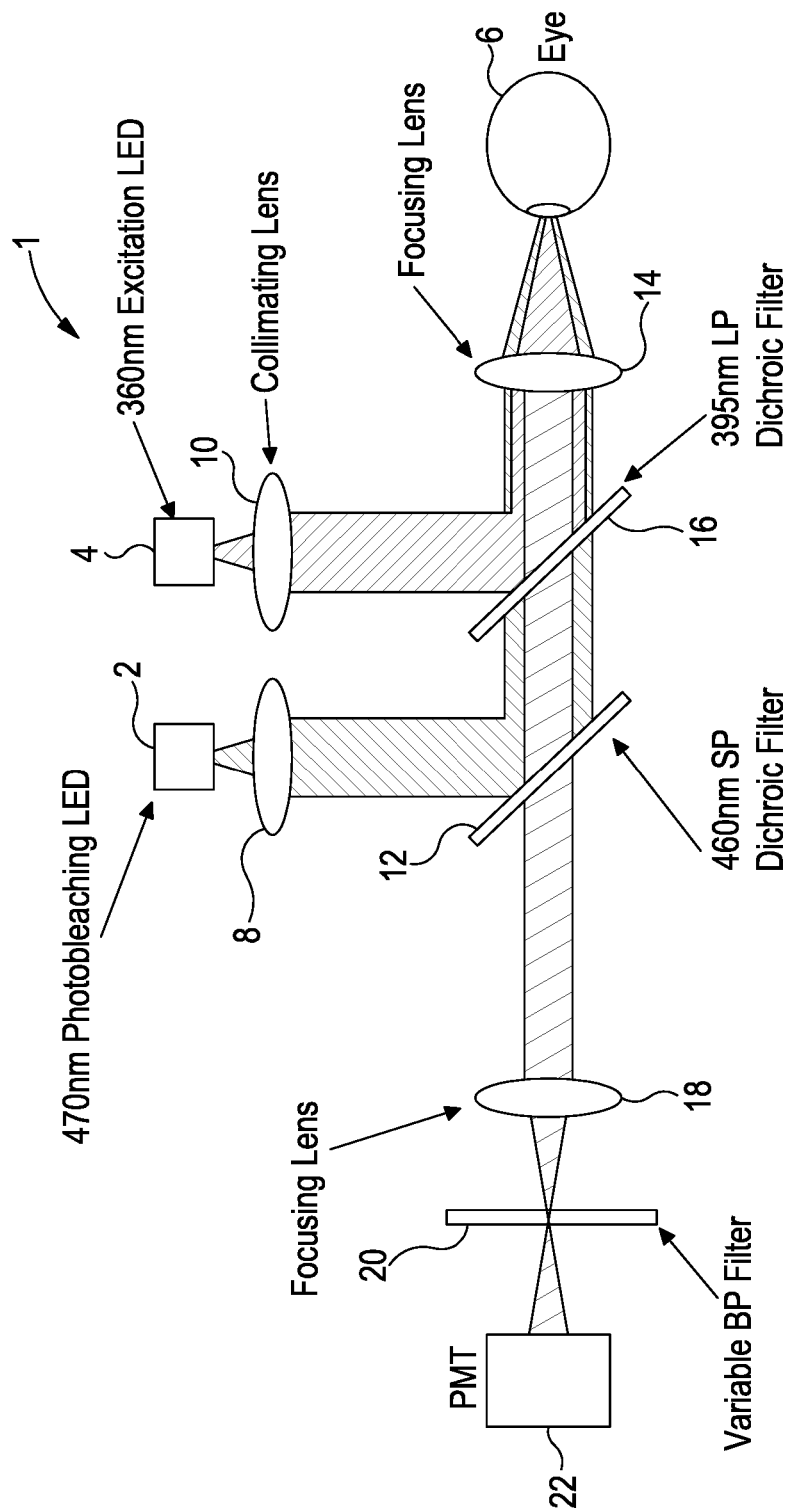
FIG. 6 is a schematic diagram of another optical system for treating and monitoring an eye.

FIG. 6 shows another system for treating and monitoring cataracts, with similar parts numbered the same as in FIG. 1. This has the same basic layout as FIG. 1. However, in this case the photobleaching wavelength is 470 nm and the excitation wavelength is 360 nm. Light from the photobleaching LED 2 is directed onto a short pass dichroic beam splitter 12 (in this case a 460 nm dichroic beam splitter) that is adapted to reflect the 470 nm treatment light along an optical path to a first focusing lens that focuses the light onto the eye 6. Light from the 360 nm excitation LED is directed onto a long pass dichroic beam splitter 16 (in this case a 395 nm dichroic beam splitter) that is adapted to reflect the 360 nm excitation light along the same optical path to the first focusing lens that focuses the light onto the eye 6.

Excitation at 360 nm allows for selective observation of the emission intensity of NFK upon manipulation of the lens system. Additionally, at 360 nm, the cornea transmits up to 80% allowing for observation of the NFK/kynurenine signal in an intact eye.

Whilst FIG. 1 shows a system in which the photobleaching wavelength is 405 nm and the fluorescence excitation wavelength is 315, and FIG. 6 shows system in which the photo-bleaching wavelength is 470 nm and the fluorescence excitation wavelength is 360 nm, other combinations of photo-bleaching wavelength and fluorescence excitation wavelength could be used.

Figure 7:
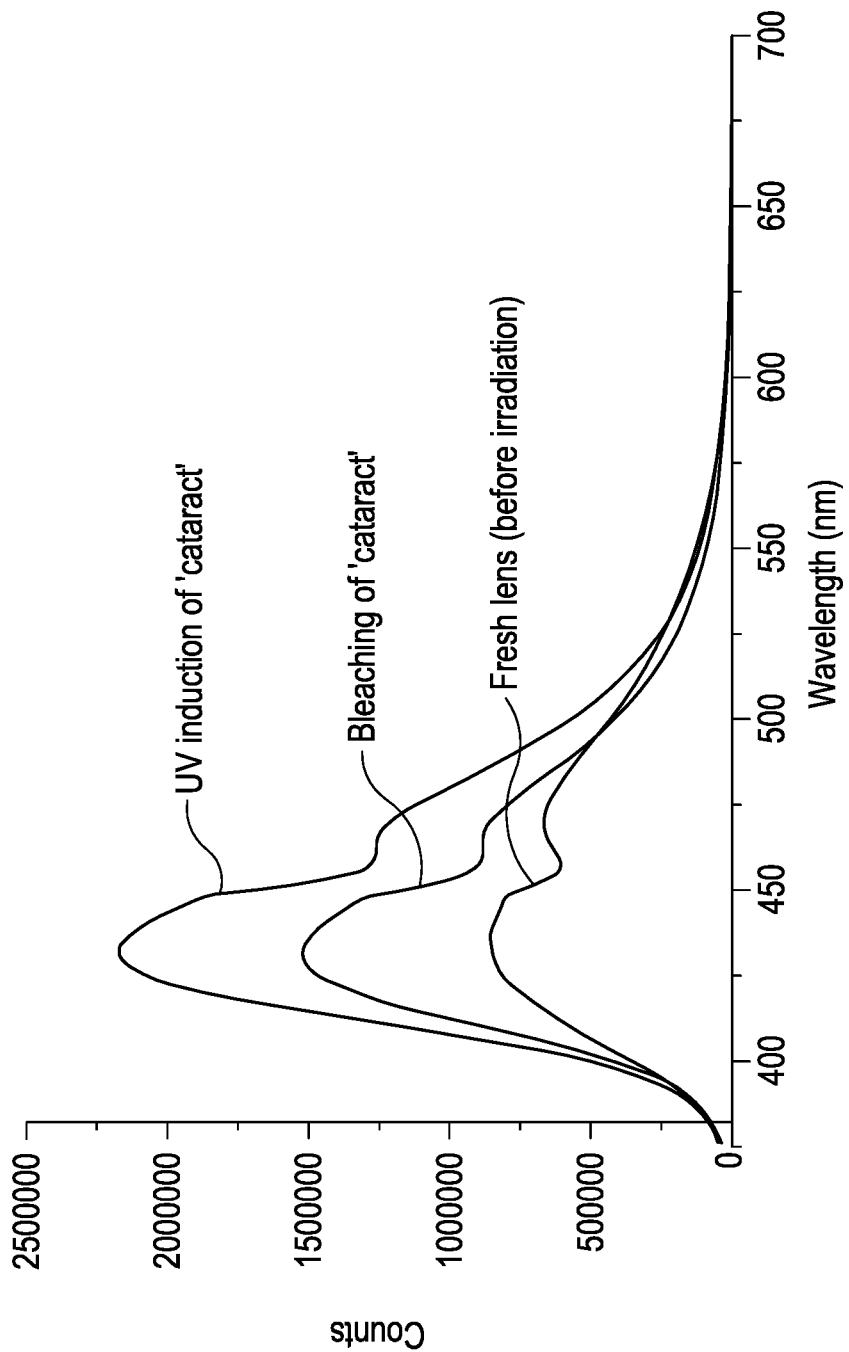
FIG. 7 shows emission spectra of a porcine lens before damage, after UV damage to induce cataract formation, and after bleaching of the cataract.

FIG. 7 shows various fluorescence spectral profiles for an extracted porcine lens before and after photo-bleaching using 405 nm irradiation wavelength. In this case, the emission spectra were taken using a fluorescence excitation of 360 nm. The spectra of FIG. 7 show that a peak at 430 nm was observed before damage inducing irradiation which corresponds to the naturally occurring kynurenines within the lens. Following damage inducing irradiation at 310 nm a 156% increase in emission intensity was observed at 430 nm indicating the photo-oxidation of tryptophan to NFK and kynurenine. Bleaching of this emission was carried out at 405 nm and induced a 30% decrease in emission intensity.

The wavelengths between 400 nm and 515 nm used to photobleach induced cataracts in porcine lenses have sufficient energy to break the single bonds between N—N, N—O and C—N. These bonds all exist in N-formyl kynurenine which fluoresces at ~430 nm and indicates the state of cataract. The energy levels for photobleaching using single photon effects at these wavelengths are between 2.4 and 3.1 eV.

Figure 8:
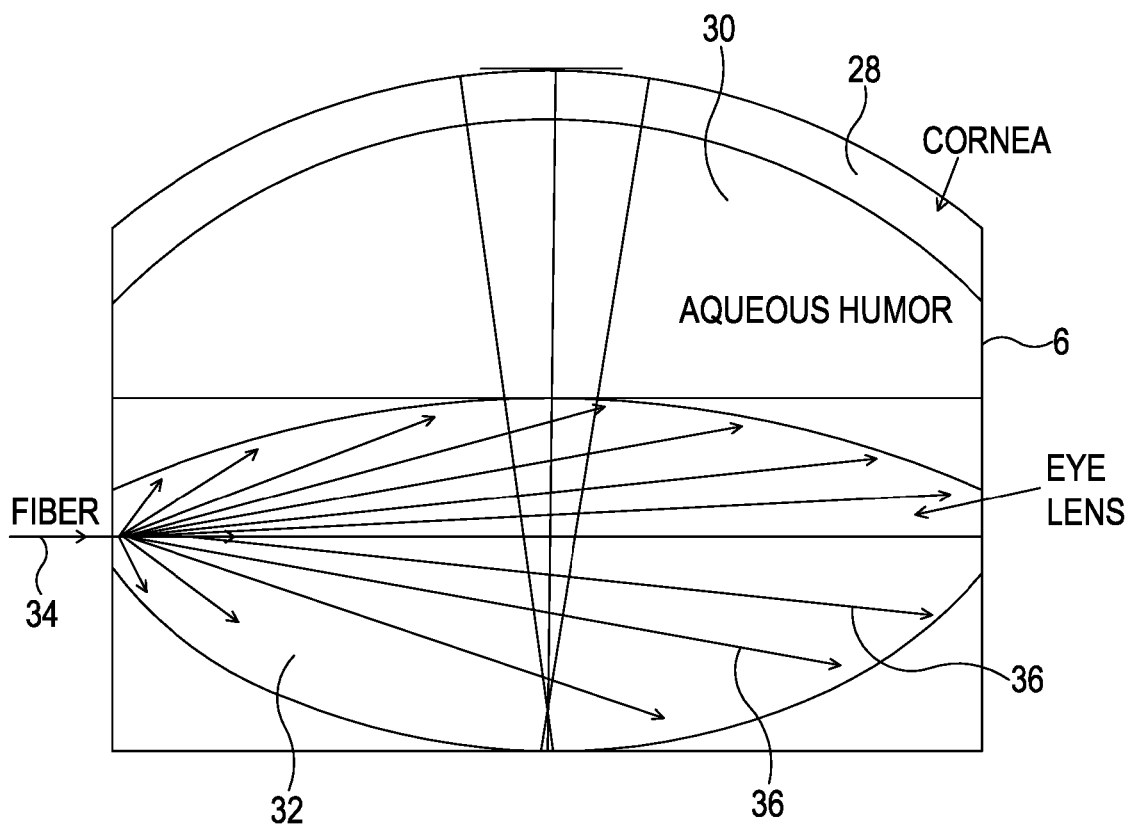
FIG. 8 illustrates schematically an eye structure with an optical fibre illuminating the lens from the side.

FIG. 8 illustrates schematically the use of a system of the invention such as those illustrated in FIGS. 1 and 6 but using an optical fibre probe to deliver light directly into the lens of an eye. In the schematic, the eye 6 includes an outer cornea 28, aqueous humor 30 and eye lens 32. An optical fibre 34 has been inserted at the side of the lens 32 to direct light into it. As suggested by rays 36 emanating from the end of fibre 34 light is spread throughout substantially the whole body of the lens. In a test on an isolated porcine lens using such an arrangement, the interior of the lens was illuminated but a screen placed about the lens (simulating the retina) was not significantly illuminated. This indicates that the method can avoid potential damage from light falling on the retina.

Figure 9:
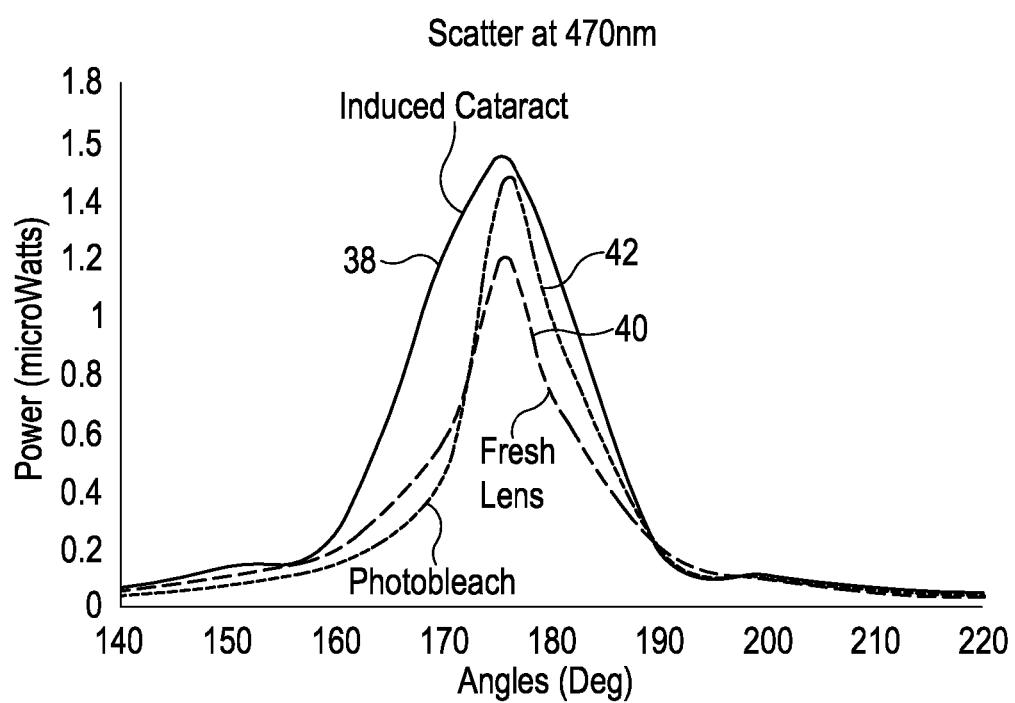
FIG. 9 shows graphically light scattering results from a porcine lens.

FIG. 9 shows graphically the results of light scattering experiments. In these experiments forward scatter through a fresh porcine lens was determined using a 470 nm LED source and a diode detector at 120 mm from the lens rotating horizontally to measure scatter power at different angle. After inducing a cataract with UV at 310 nm the scatter peak 38 shows that amount of scatter as measured by peak height has increased and the width of the peak has also increased significantly, when compared to the scatter peak 40 for the fresh lens. After photobleaching at 420 nm the width of the scatter peak for the photobleached lens 42 has reduced substantially back towards that of the fresh lens 40.

Figure 10:
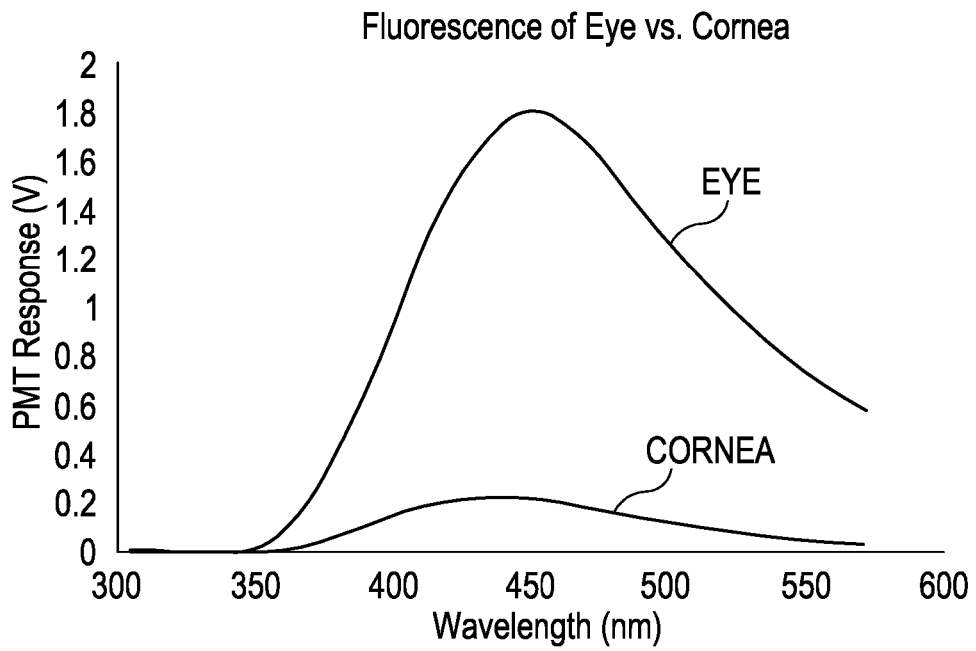
FIG. 10 shows fluorescence measurements from a porcine eye.
Figure 11:
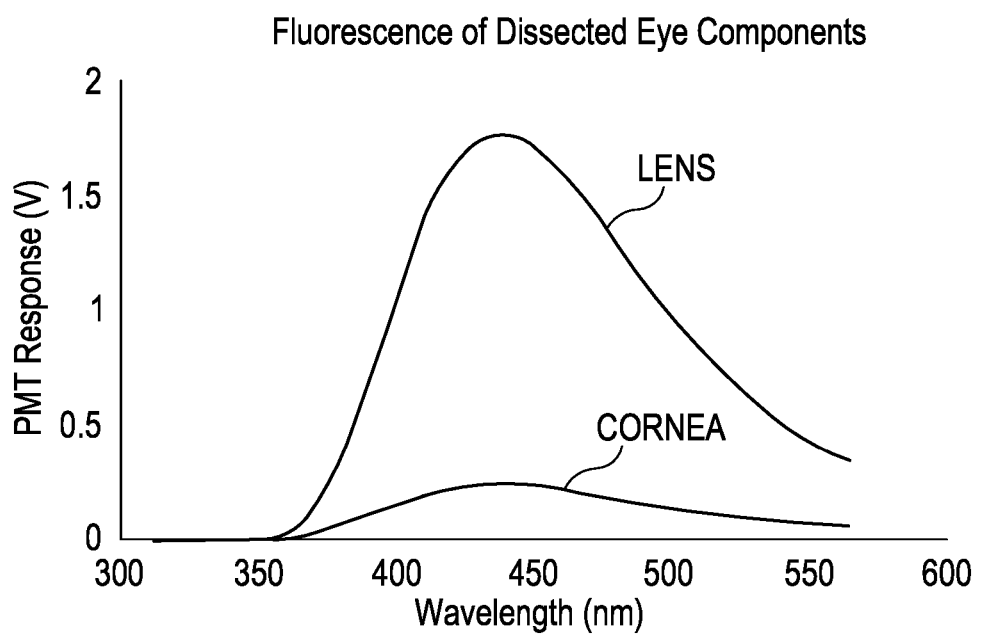
FIG. 11 shows fluorescence measurements from porcine eye components.

FIG. 10 shows graphically fluorescence results for a porcine complete eye and the cornea for the same eye when extracted and examined separately. FIG. 11 shows the fluorescence results for the lens and the cornea for the same eye when extracted and examined separately. The results show the fluorescence of the eye as a whole is not substantially affected by the cornea and the lens is the main contributor to the fluorescence of an eye. This illustrates suitability of the methods described herein for eye monitoring.

The system of the invention is very simple and compact and allows the treatment and monitoring of cataracts in vivo. This is a significant technical advance.

A skilled person will appreciate that variations of the disclosed arrangements are possible without departing from the scope of the invention. Accordingly, the above description of the specific embodiment is made by way of example only and not for the purposes of limitation. It will be clear to the skilled person that minor modifications may be made without significant changes to the operation described.

The invention claimed is:

1. A system for treating and monitoring cataracts, the system comprising:
    a non-lasing LED irradiating light source configured to irradiate an eye at a wavelength in the range of 400 nm to 520 nm to treat a cataract,
    a non-lasing LED excitation light source configured to excite fluorescence in the eye by emitting light in the range of 310 nm to 320 nm, and
    a detector and associated variable bandpass interference filter configured to detect a fluorescence spectrum stimulated by the excitation light source, thereby to simultaneously monitor emission of individual spectral components of tryptophan photo-products and/or other fluorescent post-translational modification associated with eye lens proteins,
    wherein light from the non-lasing LED irradiating source is directed onto a first dichroic beam splitter adapted to reflect the irradiating light along an optical path to a first focusing lens for focusing light onto the eye, and
    light from the non-lasing LED excitation light source is directed onto a second dichroic beam splitter adapted to reflect the excitation light along the same optical path to the first focusing lens,
    so that fluoresced light from the eye received by the first focusing lens is directed along said same optical path through the first and second dichroic beam splitters and onto the variable bandpass interference filter.

2. A system as claimed in claim 1 wherein the excitation light source is operable to emit light at 315 nm or 360 nm.

3. A system as claimed in claim 1 configured simultaneously to irradiate the eye using the non-lasing LED irradiating light source and to excite the eye using the non-lasing LED excitation light source.

4. A system as claimed in claim 1 further comprising a light guide, preferably an optical fibre light guide, to transmit light into and/or receive light from the lens of the eye in use.

5. A system as claimed in claim 1 comprising a further non-lasing light source for irradiating the eye; and a further detector for detecting scatter of light from the eye.

6. A system as claimed in claim 5 wherein the further non-lasing light source is a non-lasing LED that emits light of a wavelength of from 450 nm to 550 nm.

7. A system as claimed in claim 5 wherein the further detector comprises a diode detector.

8. A system as claimed in claim 5 wherein the further detector is rotatable about the position of the eye in use.

9. A system as claimed in claim 8 wherein the further detector is rotatable to measure scatter at different angles with respect to a direction of irradiation of said further non-lasing light source.

10. A system as claimed in claim 5 wherein the further non-lasing light source is a further LED light source arranged at an angle away from a normal of the non-lasing LED irradiating light source and the non-lasing LED excitation light source.

11. A system as claimed in claim 1 wherein the detector comprises a further focusing lens and associated photomultiplier detector.

12. A system as claimed in claim 1 wherein the detector comprises a divergent lens and diode array of detectors to enable analysis of a plurality of wavelengths simultaneously.

13. A system as claimed in claim 1 wherein the non-lasing irradiating LED light source is configured to irradiate an eye at a wavelength of 405 nm.

* * * * *